(12) United States Patent
Ueda (10) Patent No.: US 9,080,140 B2
(45) Date of Patent: Jul. 14, 2015

(54) SELECTIVE CONFORMATION OF CELL CULTURING SUPPORT LAYER

(75) Inventor: Masahiro Ueda, Kyoto (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 1023 days.

(21) Appl. No.: 12/628,850

(22) Filed: Dec. 1, 2009

(65) Prior Publication Data

US 2011/0129912 A1     Jun. 2, 2011

(51) Int. Cl.
| | | |
|---|---|---|
| C12M 1/26 | (2006.01) | |
| C12M 1/00 | (2006.01) | |
| G02B 5/00 | (2006.01) | |
| G02B 17/00 | (2006.01) | |
| C12M 1/12 | (2006.01) | |

(52) U.S. Cl.
CPC ............... *C12M 33/00* (2013.01); *C12M 23/20* (2013.01); *C12M 25/00* (2013.01); *C12M 31/00* (2013.01); *G02B 5/00* (2013.01); *G02B 17/002* (2013.01)

(58) Field of Classification Search
None
See application file for complete search history.

(56) References Cited

U.S. PATENT DOCUMENTS 6,375,903 B1 *     4/2002     Cerrina et al. ................. 422/131

FOREIGN PATENT DOCUMENTS

JP       2004000051       1/2004

OTHER PUBLICATIONS

"Diazo compound." Enclyclopaedia Britannica. Encyclopaedia Britannica Online Academic Edition. Encyclopaedia Britannica Inc. [online], 2012 [retrieved on Jul. 15, 2012]. Retrieved from the Internet< URL: http://www.britannica.com/EBchecked/topic/161940/diazo-compound?sections=161940main,161940Citations &view=print>.*
Higuchi, A et al. Photon-modulated changes of cell attachments on poly(spiropyran-co-methyl methacrylate) membranes. Biomacromolecules. 2004. 5: 1770-1774.*
"R-5.3.3 Azo, azoxy, diazo, and related compounds." IUPAC Nomenclature of Organic Chemistry [online]. Blackwell Scientific publications, 1993 [retrieved on Sep. 19, 2014]. Retrieved from the Internet< URL: http://acdlabs.com/iupac/nomenclature/93/r93_377.htm> pp. 1 and 4.*
Sasaki, YC et al. Observation of nanometer-level structural changes by the trans-cis transition of an azobenzene derivative monolayer with a radioactive tracer. Langmuir. 1996. 12: 4173-4175.*
Yamamoto, T et al. Photonic manipulation of topological defects in liquid-crystal emulsions doped with azobenzene derivatives. Thin Solid Films. 2006. 509: 81-84.*
Kunihiro Ichimura, et al "Light-Driven Motion of Liquids on a Photoresponsive Surface" Science, vol. 288,(2000), pp. 1624-1626. Online: http://www.incom.co.jp/productnavi/index.php/product/34363 "Visible light spot radiation device: Bio Spot Light", Accessed Aug. 24, 2009.
George M. Whitesides, et al "Wet Chemical Approaches to the Characterization of Organic Surfaces: Self-Assembled Monolayers, Wetting, and the Physical-Organic Chemistry of the Solid-Liquid Interface" The Longmuir Lectures, vol. 6, No. 1, 1990, pp. 87-96.
Colin D. Bain, et al "Modeling Organic Surfaces with Self-Assembled Monolayers" Agnew. Chem. Int. Ed. Engl. 28, (1989) No. 4, pp. 506-512.
L. M. Siewierski, et al "Photoresponsive Monolayers Containing In-Chain Azobenzene" Langmuir (1996) 12, pp. 5838-5844.
G. Moeller, et al "Controlling Microdroplet Formation by Light" Langmuir vol. 14, No. 18, Sep. 1, 1998; pp. 4955-4957.
Sang-Keun Oh, et al "Self-Assembled Monolayers Derived from Calix[4]resorcinarenes Exhibiting Excellent Desorption-Resistance and Their Applicability to Surface Energy Photocontrol" Chemistry Letters 1999 pp. 349-350.
Masanori Fujimaki, et al "Marcrocyclic Amphiphiles. 3. Monolayers of O-Octacarboxymethoxylated Calix[4] resorcinaresnes with Azobenzene Residues Exhibiting Efficient Photoisomerizability" Langmuir 1998, vol. 14, No. 16, pp. 4495-4502.
Eiichi Kurita, et al "Macrocyclic amphiphiles, Part 2. Multi-point adsorptivity of the crown conformer of calix[4] resorcinarenes and their derivatives on surfaces of amorphous polar substrates" Journal of Materials Chemistry, vol. 8, No. 2, 1998, pp. 397-403.

* cited by examiner

*Primary Examiner* — Allison Fox
*Assistant Examiner* — Susan E Fernandez
(74) *Attorney, Agent, or Firm* — Dorsey & Whitney LLP (57) ABSTRACT

Embodiments described herein relate to in vitro cell culture. Embodiments include a substrate having a support layer that includes support molecules having a first region configured to bind to the substrate and having a photo-responsive region configured to change conformation between at least two conformations. In a first conformation of the photo-responsive region, the support molecules are configured to be more accessible to cells. In a second conformation of the photo-responsive region, the support molecules are configured to be less accessible to cells.

17 Claims, 3 Drawing Sheets

SELECTIVE CONFORMATION OF CELL CULTURING SUPPORT LAYER

TECHNICAL FIELD

Embodiments described herein can broadly be used in technical fields implicating cell culturing systems to facilitate culturing and harvesting of cells.

BACKGROUND

Many types of cells can be cultured in vitro in suspension or as adherent cultures. Some cells, such as blood cells, naturally live in suspension, without being attached to a surface. In contrast, most cells derived from solid tissues are adherent. Some examples of adherent cells that can be cultured include epithelial cells, hematopoietic cells, mast cells, neurocytes, hepatocytes, hepatic parenchymal cells, bone marrow cells, osteoblasts, fibroblasts, and epidermal cells. Many types of adherent stem cells can also be grown in culture. Some examples of stem cells include pluripotent stem cells, induced pluripotent stem cells, embryonic stem cells, adult stem cells, and multipotent and induced multipotent stem cells.

Generally, adherent cells are grown on a surface, such as the surface of a cell culture dish or on a microcarrier. Adherent cells naturally adhere to one another and to surfaces, which in some ways mimics the in vivo lifestyle of the cells. Often the surface is coated with extracellular matrix components such a collagen and/or elastin to increase adhesion properties and provide other signals needed for growth and differentiation.

When cultured cells are ready for harvesting, chemical means such as enzymes (e.g., collagenase) and/or physical means such as glass capillary colony cutters have generally been used to separate the cells from the surface. However use of chemicals, enzymes, and/or physical means to separate cultured cells from the surface can damage the cells. Additionally, harvesting can damage the cells if the cells are not separated from the surface prior to harvesting. Further, these chemical and physical methods can be time consuming, tedious, and costly.

SUMMARY

In one embodiment, the present disclosure describes an apparatus for cell culture. In one aspect, the apparatus includes a substrate and a support layer at least partially coating the substrate. In one aspect, the support layer includes support molecules having a first region configured to bind to the substrate and having a photo-responsive region configured to change conformation responsive to irradiation from at least a first optical energy source. In a first conformation of the photo-responsive region, the support molecules are in a more hydrophobic state configured to be more accessible to cells. In a second conformation of the photo-responsive region, the support molecules are in a more hydrophilic state configured to be less accessible to cells.

In another embodiment, a method for culturing cells is described. The method can include culturing a plurality of cells on a substrate, the substrate having a support layer at least partially coating the substrate, wherein the support layer includes support molecules having a first region bound to the substrate and having a photo-sensitive region. In one aspect, the photo-sensitive region has a first conformation wherein the support molecules have a first, more hydrophobic state that is accessible to one or more cells. In one aspect, the method includes radiating a first optical energy onto at least some of the support molecules so that the photo-responsive region of the at least some support molecules adopts a second conformation, wherein the support molecules have a second, more hydrophilic state that is less accessible to the one or more cells.

In yet another embodiment, a composition for use in culturing cells is described. In one aspect, the composition can include a first region configured to bind to a substrate and a photo-responsive region configured to change conformation between at least a first conformation and a second conformation responsive to an optical energy source. In the first conformation of the photo-responsive region, the composition can adopt a more hydrophobic state configured to be more accessible to cells. In the second conformation of the photo-responsive region, the composition can adopt a more hydrophilic state configured to be less accessible to cells.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments herein are directed to providing a cell culture environment that allows the cells to grow on a support that can readily allow harvesting the cells without damage to the cells. Embodiments described herein provide compositions, apparatuses, and methods for culturing and harvesting cells without use of conventional chemical and physical harvesting methods. This is accomplished by modifying the substrate on which cells are cultured to include a support layer that provides a biocompatible surface for culturing cells that facilitates separation of the cells from the substrate.

In one embodiment, the present disclosure describes an apparatus for cell culture. In one aspect, the apparatus includes a substrate and a support layer at least partially coating the substrate. In one aspect, the support layer includes support molecules having a first region configured to bind to the substrate and having a photo-responsive region configured to change conformation responsive to irradiation from at least a first optical energy source. In a first conformation of the photo-responsive region, the support molecules are in a more hydrophobic state configured to be more accessible to cells. In a second conformation of the photo-responsive region, the support molecules are in a more hydrophilic state configured to be less accessible to cells.

In one aspect, a substrate can be any surface used to culture cells, such as but not limited to a culture container (e.g., petri dish), a culture flask, a culture bag, a culture plate, tissue engineering scaffolds (e.g. tubular structures, lattice configurations, three-dimensional elements) among others. Materials of the substrate can be, but are not limited to, glass, quartz, polycarbonate, plastic, silicon, and the like. Other materials and types of substrates will be readily apparent to those skilled in this area.

In some embodiments, the support layer at least partially coats the substrate. That is, the support layer can be applied to the substrate so as to completely coat the substrate. In such a case, the support layer facilitates separation of the cultured cells from the entire substrate. Alternatively, the support layer can partially coat the substrate. Nevertheless, the support layer can facilitate separation of cultured cells from the support by separating part of the cells so as to allow the rest of the cells to be peeled from the surface. In another embodiment, the support layer can be applied to the substrate in a patterned arrangement for patterned cell culture. For example, the substrate can be applied to the substrate in a linear, substantially linear, or curvilinear pattern so as to facilitate growing cells in a linear, substantially linear, or curvilinear shape.

In one aspect, the support layer can include support molecules that facilitate culturing of cells and extraction of adherent cells from a surface. The use of the term "support molecule" refers to molecules that modifies the substrate and provide a layer on one or more surfaces upon which to culture cells. The term "support" when used in reference to molecules is not intended to refer to any particular structure or characteristic of the molecules themselves.

Support molecules have at least a first region configured to associate with the substrate (e.g., covalently bind or hydrogen bond) and a photo-responsive region that is at least partially exposed. The photo responsive region is configured such that one or more cells may associate with the partially exposed portion of the support molecules during cell culture. The photo-responsive region is also configured such that the one or more cells may be readily separated from the support molecules when it is time to harvest the cultured cells.

In one aspect, the photo-responsive region is configured to change conformation in response to irradiation. For instance, the photo-responsive region can have a first conformation that cells can associate with and a second conformation that is less amenable to cell attachment. In one aspect, the first conformation can be used during cell culture and the second conformation can be used to facilitate separation of cultured cells from the support molecules and thus the substrate.

In one aspect, the photo-responsive region can be configured to change conformation between at least a more hydrophobic state and more hydrophilic state in response to irradiation from at least a first optical energy source. As used herein, the terms "hydrophobic" and "hydrophilic" are used broadly in accordance with their common meaning. For example, the term "hydrophobic" translates literally to water fearing. Substances that are hydrophobic tend to favor nonpolar and/or inaqueous environments. In contrast, the term "hydrophilic" translates literally to water loving. Substances that are hydrophilic tend to favor polar and/or aqueous environments.

The terms hydrophobic and hydrophilic are used herein in conjunction with terms like "more" and "less" so that it is clear that the disclosure herein is not limited to the first conformational state being hydrophobic per se or the second conformational state being hydrophilic per se. Rather, the second conformational state is generally "more hydrophilic" than the first conformational state. Or in other terms, the second conformational state is generally "less hydrophobic" than the first conformational state.

When the photo-responsive region has the more hydrophobic state, the photo-responsive region has a first conformation that is more accessible and/or suitable for association with and optionally adherence by cultured cells. For example, in the hydrophobic state, the photo-responsive region can present hydrophobic phenyl groups to the cells that are compatible with the lipid membrane of the cells and that my mimic amino acid side chains encountered by cells in the in vivo extracellular matrix. When the photo-responsive region has the more hydrophilic state, the photo-responsive region has a second conformation that is less accessible and/or less conducive to association with and optionally adherence by cultured cells. Without being tied to one theory, it is believed that the more hydrophilic state is less conducive to association with the cultured cells because the more hydrophilic state preferably binds water that is present in the media. Moreover, it is believed that the more hydrophilic state is less conducive to association with the lipid membrane of the cells.

Thus, during culturing, the photo-responsive region of at least some of the support molecules of the support layer has a more hydrophobic state allowing at least partial association and optionally adherence between the cultured cells and the support molecules. Association between the cultured cells and the support molecules can be driven by various forces including, but not limited to noncovalent associations such as, but not limited to, hydrogen bonding, ionic bonding, Van der waals forces, hydrophobic interactions, and electrostatic interactions.

In one embodiment, the photo-responsive region of the support molecules includes one or more groups that undergo a conformational change upon irradiation from the optical energy source. In one embodiment, the photo-responsive region of the support molecules includes one or more groups that can undergo a cis-trans isomerization reaction (i.e., cis to trans or trans to cis) in response to irradiation from the optical energy source. In one embodiment, the support molecules include an azobenzene functional group that can undergo a cis-trans isomerization, which results in a conformational change that can cause the support molecules to switch from a state that displays a relatively hydrophobic surface that is conducive to adherent cell association to a relatively hydrophilic state that displays hydrophilic groups that are less conducive to adherent cell association.

Additional photo-reactive transformations that can be utilized in the present disclosure include, but are not limited to, ring-opening or closing reactions, pericyclic reactions, intramolecular hydrogen transfers, intramolecular group transfers, dissociation processes and electron transfers. For example, photo-reactive spiro compounds are known to undergo reversible ring opening reactions in response to irradiation. Similarly, photo-reactive diarylethenes are known undergo ring-opening reactions in response to irradiation. In addition, some photoreactive quinones (e.g., phenoxynaphthacene quinone) have phenyl groups that can migrate from one oxygen atom to another in response to irradiation. Any of the above cited examples can result in a conformational and/or chemical environment change that can cause support molecules to switch from a state that is conducive to adherent cell association to a state that is less conducive to adherent cell association.

Embodiments herein contemplate that when the photo-responsive region of the support molecules is in the first conformational state (i.e., more hydrophobic state), the support molecules present chemical functional groups that are conducive to association with adherent cells. For example, the support molecules having the photo-responsive region in the first conformational state can present phenyl groups that are conducive to association with the lipid portion of the phospho-lipid cell membrane and/or the support molecules can present groups that are conducive to association with the phospho portion of the phospho-lipid cell membrane. When the photo-responsive region conforms to the second conformational state (i.e., more hydrophilic state), the support molecules can present functional groups (e.g., carboxylate groups) are less conducive to association with the cultured cells. For example, the support molecules in the second conformational state can present polar functional groups (e.g., carboxylate groups) are less conducive to association with the lipid membrane portion. In addition, polar functional groups can be more attracted to water than to the outer phospho portion cellular membrane, which also tends to disrupt associations between the cultured cells and the support molecules.

In some embodiments, the photo-responsive region may be configured with more than photo-reactive group such that the support molecule can have more than two conformations. For example, a first photo-reactive group can be an azobenzene and a second photo-reactive groups can be a diarylethene. Moreover, the photo-reactive groups can be configured such that they are responsive to different wavelengths of light and/or different intensities of irradiation by tailoring the chemical environment around the photo-reactive groups. This can allow the support molecules to adopt a number of conformations having different affinities for the cultured cells.

In one aspect, each conformation of the support molecules can have different polarization or phases or grades of polarization, with some grades being more hydrophobic and some grades being more hydrophilic.

In all of these embodiments, the second conformational state (i.e., more hydrophilic state) increases the "wettability" (i.e., the hydrophilicity) of the support layer so that cultured cells are more easily separated from the support layer. This is due to a change in conformation of the photo-responsive region, which causes the support molecules to become less or more hydrophobic/hydrophilic depending on the conformation when manipulated by an optical energy source. When the support molecules are less hydrophilic, the support molecules are more able to adhere to cells. When the support molecules are more hydrophilic, the hydrophobic portions of the support molecules are less available and less susceptible to bonding with the membranes of the cultured cells and the hydrophilic portions of the support molecules are more likely to bond to water than to the cells.

This is also referred to as "wettability" of the support layer since the support layer is more "wet" due to water molecules being bonded to the hydrophilic portions of the photo-responsive region. This wettability of the support layer eases harvesting of cells because the cultured cells are less conducive to association with the support molecules when the support molecules are in the more hydrophobic state. When the cells are harvested, the cultured cells are easily peeled off of the wet support layer without causing damage to the cultured cells. Further, because the methods disclosed herein facilitate harvesting cells from cell culture and/or facilitate cell transfer from one culture to another, these methods also decreases the costs of cell culturing, requiring fewer resources and energy.

In some embodiments, a conformation of the photo-responsive region not only affects the conformational state, but may also have a steric effect that contributes to cell adherence. When the photo-responsive region is in the first conformation that is more conducive to cell adherence than the second conformation, the first conformation may also have chemical structure that is more accessible to the cultured cells. When the photo-responsive region is in the second conformation, the photo-responsive region may have a chemical structure where sites to which the cell would normally adhere are now less accessible, making it less conducive for the cell to adhere. For example, the phenyl groups of the azobenzene structure discussed herein may be sterically accessible when the photo-responsive region is in the first conformation. In contrast, the conformation of the support molecules changes when the cis-trans isomerization is stimulated by irradiation, which can, for example, make the phenyl groups sterically inaccessible to the cultured cells.

In view of the foregoing, compositions for use in cell culture, apparatuses for use in cell culture, and methods for cell culture will now be described in further detail with reference to the drawings.

Figure 1:
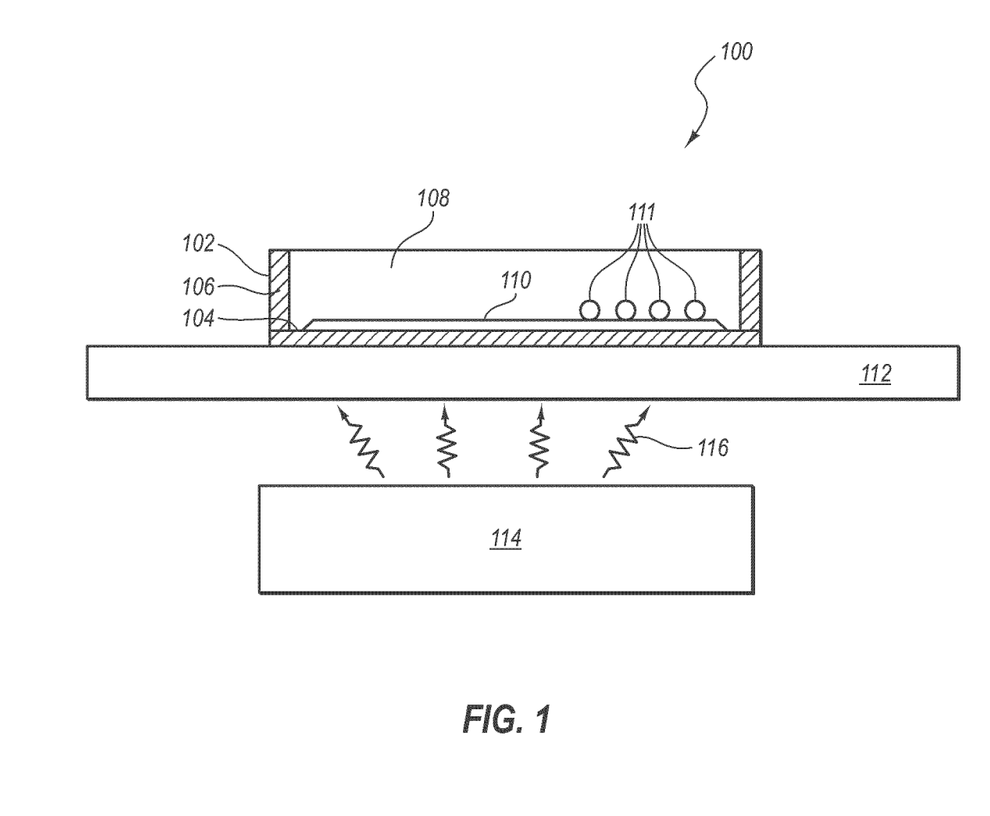
FIG. 1 is a schematic diagram of an illustrative apparatus for cell culture.

FIG. 1 is a schematic diagram of an illustrative apparatus for cell culture. The apparatus 100 has a substrate 102. The substrate 102 can be any surface used to culture cells, such as a culture container (e.g., petri dish), a culture flask, a culture bag, a culture plate, and the like. Materials of the substrate can be, but are not limited to, glass, quartz, polycarbonate, plastic, silicon, and the like. Other materials and types of substrates will be readily apparent to those skilled in the technical area and/or described herein. In the embodiment of FIG. 1, the substrate 102 is shown as a cross-section of a petri dish, which is commonly used to culture cells. In one embodiment, a bottom surface 104 of the substrate 102 is at least partially transparent to allow light to pass through the bottom surface 104. In another embodiment, a side surface 106 of the substrate 102 is at least partially transparent to allow light to pass the side surface 106. However, it is not required that either the bottom surface 104 or side surface be partially or completely transparent so long as light is able to reach the substrate 102 in some manner. For example, the bottom surface 104 and side surface 106 may both be opaque but the substrate 102 may have a top opening 108 that allows light to reach the bottom surface 104 from above the substrate 102.

FIG. 1 shows a support layer 110 at least partially coating the substrate 102. In one embodiment, the support layer 110 can be applied to the substrate 102 such that the support layer 110 forms a substantially uniform coating over the substrate 102. In another embodiment, the support layer 110 can be applied to the substrate 102 such that the support layer 110 forms a discontinuous coating over the substrate 102. For example, some portions of the substrate 102 can be coated while others are left uncoated.

The support layer 110 is generally a single layer of support molecules. Note that FIG. 1 is not drawn to scale as the support molecules generate a support layer 110 usually having a thickness of about 1 nm to about 20 nm, about 1 nm to about 10 nm, or about 1 nm to about 5 nm. The support molecules will be described in further detail below. FIG. 1 illustrates schematically a plurality of cells 111 that are placed on the support layer 110 to be cultured.

The substrate 102 can be rested on a platform 112. In one embodiment, the platform 112 is any structure that is able to support the substrate 102. The platform 112 can be a table, bench, or counter. In another embodiment, the platform 112 is used to raise the substrate 102 sufficiently so that an optical device 114 can be placed underneath the platform 112, and, hence, the substrate 102. The optical device 114 radiates optical energy 116 to the support layer 110. In one embodiment, the platform 112 is a table with a clear surface (e.g., glass, plastic), and the optical device 114 is provided underneath the table. However, as discussed above, the optical device 114 may be placed in any relationship to the substrate 102 (such as underneath, at the side, above), so long as the optical energy 116 is able to reach the support layer 110.

The optical device 114 is configured to selectively radiate optical energy 116 on the substrate 102 at the desired time. In some embodiments, the photo-responsive region is activated using an optical device 114 including, but not limited to, a mercury-vapor lamp, a xenon-mercury lamp, a high intensity discharge lamp, an LED lamp, and the like. Further, the optical device 114 can be configured to radiate only a portion of the substrate 102. For example, if only a portion of the substrate 102 contains cells that are mature enough to harvest, the optical device 114 can be radiate only the portion of the substrate 102 that contains the mature cells. In one embodiment, the optical device 114 can include an array of several of optical elements that are situated above or under the substrate 102 so as to substantially cover the same square area as the support layer 110. In such a configuration, each optical element 114 can be operated independently of the others so that one or more portions of the substrate 102 can be radiated independently of each other.

Figure 2:
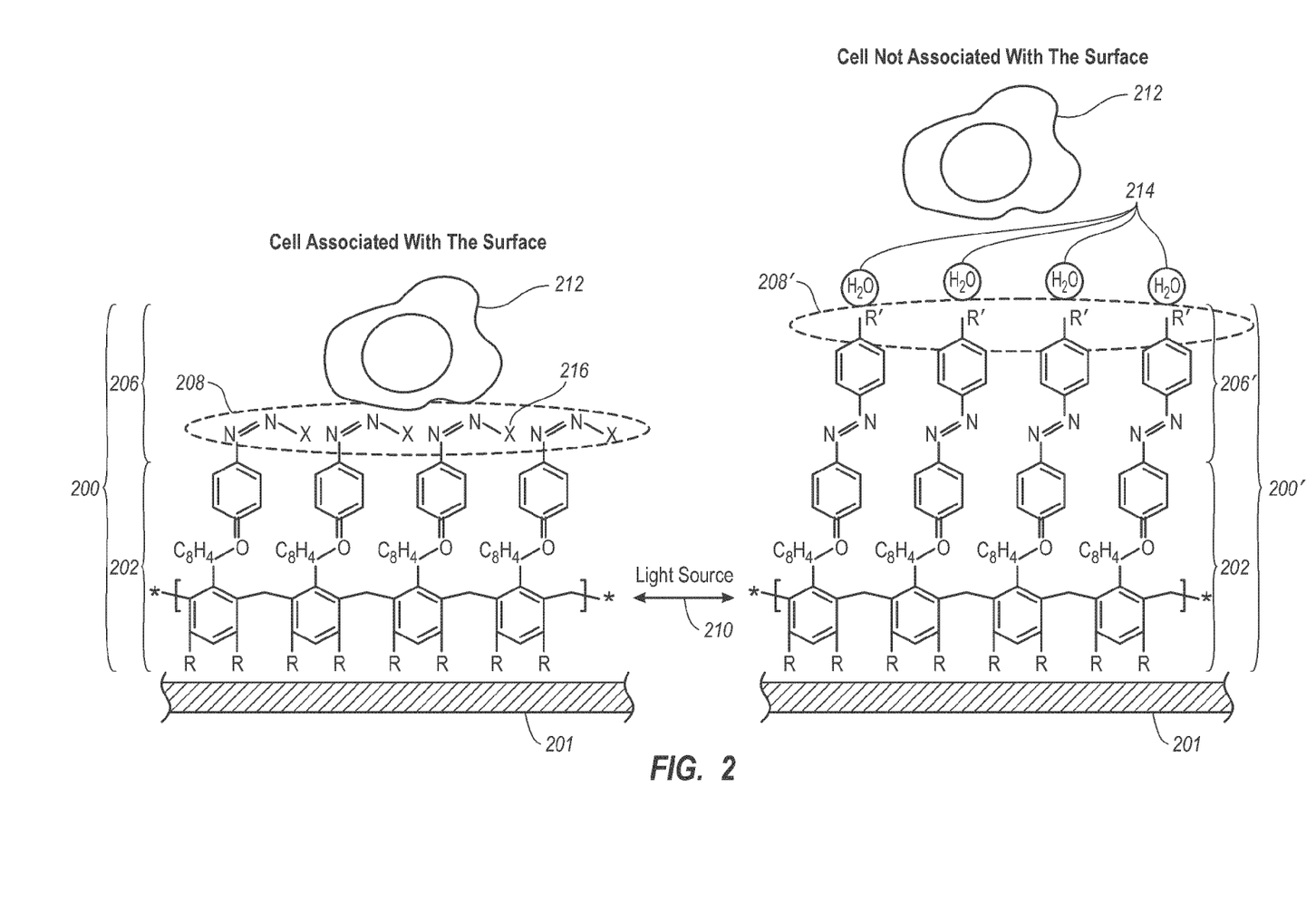
FIG. 2 shows a schematic of an illustrative support molecule, a chemical operation of the support molecule upon irradiation by an optical energy source, and an interaction between a cell and the support molecule when the conformation of the support molecule changes.

FIG. 2 shows a schematic of an illustrative support molecule, a change in conformation of the support molecule upon irradiation by an optical energy source, and an interaction between a cell and the support molecule when the conformation of the support molecule changes. In a non-limiting embodiment shown in FIG. 2, the support molecules 200 shown on the left have a first region 202 configured to bind to a substrate 201 and a photo-responsive region 206. The support molecule 200 on the left is shown in a first conformation. In contrast, the support molecule 200' on the right has a first region 202 bound to the substrate 201, and a photo-responsive region 206' in a second conformation due to irradiation by a first optical energy source 210. The numerals for support molecule 200 and support molecule 200' are used to indicate that the conformation of the support molecule has changed.

The photo-responsive region 206 is configured to selectively transition between at least a first conformation 208 (indicated by the dashed area on the left) and a second conformation 208' (indicated by the dashed area on the right) upon irradiation from at least the first optical energy source 210. The photo-responsive region 206/206' includes one or more polar groups that alter conformation from the first conformation 208 to the second conformation 208', and vice versa. As shown on the left, X 216 represents this functional group is shown on the right panel. In some embodiments, the support molecule may have different or additional functional groups that have other functionalities.

When the photo-responsive region 206 has the first conformation 208, the support molecules 200 have a first conformation that is accessible to and/or capable of adhering to cultured cells. This is shown in FIG. 2 on the left by a cell 212 that is adhered to the photo-responsive region 206 having the first conformation. As discussed in greater detail above, it is believed that the support molecules 200 having the first conformation 208 may mimic interactions that cells encounter in the extracellular matrix. For example, without being tied to a particular theory, it is believed that the support molecules 200 having the first conformation 208 are able to associate with the cell 212 because of favorable interactions between the cell membrane and the phenyl and/or the azo groups, which may mimic interactions between cells and proteins and amino acid side chains encountered in the extracellular matrix.

When the photo-responsive region 206' has the second conformation, the support molecules 200' are more hydrophilic than the first conformation 208, making the support molecules 200' less accessible and/or less conducive to adhering to cultured cells. This is shown in FIG. 2 on the right by the support molecules 200' being more likely to bond to water molecules 214 and less likely to adhere to cells 212 so that the cell 212 being unadhered, detached, or disconnected from the support molecules 200' having the second conformation 208'.

The embodiment of FIG. 2 shows one example of altering conformation of the photo-responsive region 206/206' using a cis-to-trans transformation of the support molecule 200/200'. The support molecule 200/200' shown in FIG. 2 is reproduced below:

The support molecule 200/200' shown in FIG. 2 is an azobenzene compound. As discussed elsewhere in this application, additional photo-reactive groups that can be utilized herein include, but are not limited to, spiro compounds, diarylethenes, quinones, and the like. Additional photo-reactive transformations that can be utilized in the present disclosure include, but are not limited to, ring-opening or closing reactions, pericyclic reactions, intramolecular hydrogen transfers, intramolecular group transfers, dissociation processes, electron transfers, and the like.

The azobenzene compound is a crown conformer of ocarboxymethylated calix[4]resorcinarene (CRA-CM) bearing four p-octylazobenzene residues at one of the rims of the cyclic skeleton. CRA-CM is a macrocyclic amphiphile (including the R group) forms the first region 202 that binds to the substrate (see FIG. 1). The azobenzene moieties (including the R' group) form the photoresponsive region 206/206'. The CRA-CM form a rigid cylindrical macrocycle that tethers the azobenzene moieties and can be densely packed into a single-molecule support layer.

The azobenzene moieties (i.e., the photo-responsive region 206/206') isomerizes upon irradiation of a certain wavelength of an optical energy source. The azobenzene moieties have polar groups R' that switch polarity from a first conformation 208 to a second conformation 208' upon irradiation by the optical energy source.

In one embodiment, the support layer having support molecules of an azobenzene compound may be prepared by immersing a culture container (e.g., an aminosilylated silica plate) in a dilute solution of CRA-CM, yielding a robust monolayer of support molecules with dense packing. In one embodiment, the thickness and uniformity of the coating can be measured using a stylus-type film thickness meter. In another embodiment, infrared absorption spectroscopy can be used to determine whether the coating is formed on the substrate without any deterioration of the chemical components (i.e., without deterioration of the coating material and/or the substrate). In one embodiment, the substrate and the support layer can be sterilized using, for example, gamma irradiation or ethylene oxide. The substrate and the support layer can be stored in a dry, sterile state. The support layer is substantially stable on the substrate under culture conditions.

In all of these embodiments, the second conformational state (i.e., more hydrophilic state) increases the "wettability" of the support layer 200/200' so that cultured cells 212 are more easily separated from the support layer. This is due to a change in conformation of the photo-responsive region 206/206', which can cause the support layer 200/200' to become less or more hydrophobic/hydrophilic depending on the conformation when manipulated by an optical energy source.

In some embodiments, a conformation of the photo-responsive region 206/206' not only affects the conformational state of the support layer 200/200', but may also have a steric effect that contributes to cell adherence. When the photo-responsive region 206 is in the first conformation that is more conducive to cell adherence than the second conformation, the first conformation may also have a chemical structure that is more accessible to the cultured cells. This is shown in FIG. 2 by the diazo functional group N=N being located on top of the support molecule 200 and exposed to be accessible to a cell 212. When the photo-responsive region 206' is in the second conformation, the photo-responsive region 206' may have a second chemical structure where sites to which the cell 212 would normally adhere are now less accessible, making it less conducive for the cell 212 to adhere. This is shown in FIG. 2 by the polar groups R' being on the top of the support molecule 200' and exposed to be accessible to water molecules 214, while the diazo functional group N=N become less accessible.

In one non-limiting embodiment, the support molecule shown in FIG. 2 undergoes transformation from cis isomer to trans isomer upon irradiation of a light having a wavelength of about 436 nm (blue light). Other support molecules can be engineered to absorb almost any wavelength of light depending on the type and chemical context of the photo-reactive group. Illustrative wavelengths may be about 100 nm to about 400 nm, 150 nm to about 400 nm, 200 nm to about 400 nm, 250 nm to about 400 nm, 300 nm to about 400 nm, 350 nm to about 400 nm, or about 400 nm to about 600 nm, about 400 nm to about 500 nm, or about 420 nm to about 470 nm, or about 430 nm to about 470 nm.

In particular, the optical device radiates the photo-responsive region of at least some of the support molecules of the support layer. In one embodiment, the optical device irradiates a light in a wavelength of about 400 nm to about 500 nm, or about 420 nm to about 470 nm, or about 430 nm to about 440 nm, as illustrative examples. In one embodiment, the optical device irradiates a light having a power of about 1 $mW/cm^2$ to about 100,000 $mW/cm^2$, or about 10 $mW/cm^2$ to about 10,000 $mW/cm2$, or about 100 $mW/cm^2$ to about 1,000 $mW/cm^2$, as illustrative examples. In one embodiments, the optical device 114 irradiates a light for about 0.1 to about 10,000 s, or about 1 s to about 1,000 s, or about 10 s to about 100 s, as illustrative examples. In one embodiment, the optical device irradiates a light at a distance from the support layer of about 1 cm to about 200 cm, or about 5 cm to about 100 cm, or about 25 cm to about 50 cm, as illustrative examples. In each of these examples, the entire support layer does not have to be irradiated; rather an optical element can irradiate only a portion of the support layer at the wavelength, power, time period, and/or distance as illustratively described above. Further various combinations of wavelength, power, time period, and/or distance from the substrate may be applied to trigger the photo-responsive region to conform from the first conformation to the second conformation.

In some embodiments, the photo-responsive region is activated using an optical device including, but not limited to, a mercury-vapor lamp, a xenon-mercury lamp, a high intensity discharge lamp, an LED lamp, and the like. Various optical devices are commercially sold and can be readily adapted to be included in an apparatus of this disclosure. In one embodiment, when the optical device is a matrix of optical elements, each optical element could be an LED element disposed at a particular coordinate, the matrix being disposed below the substrate so that the LED elements can be independently operated. A technician simply need activate the LED elements of coordinates corresponding to mature cultured cells to trigger the conformation for support molecules in that particular coordinate. This is one example of an optical device configured to irradiate a portion of the support molecules independently from another portion of the support molecules.

Figure 3:
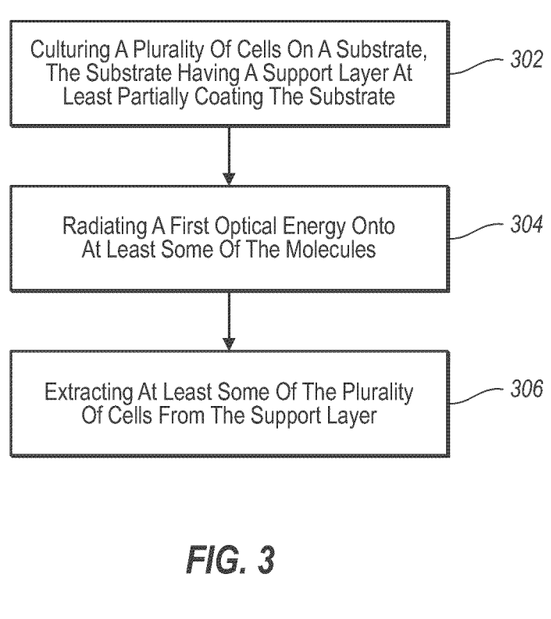
FIG. 3 shows an illustrative method for culturing cells.

FIG. 3 is an illustrative method for culturing cells. The method includes at 302, culturing a plurality of cells on a substrate. As discussed above with reference to FIG. 1, the substrate has a support layer at least partially coating the substrate, the support layer comprised of support molecules. As discussed above with reference to FIG. 2, the support molecules have a first region bound to the substrate and have a photo-sensitive region that has a more hydrophobic state that is accessible to and/or capable of adhering to one or more cells.

Various types of adherent cells can be cultured including, but not limited to, stem cells, osteocyte, epidermal cells, organ cells (e.g., blood vein cells, vascular cells, liver cells (i.e., hepatocytes), cardiac cells, etc), or other tissue engineering cells, and the like. Additional examples of adherent cells include, but are not limited to, epithelial cells, ciliated epithelial cell, chondrocyte (e.g., fibrocartilage, elastic cartilage), osteoblasts, osteocytes, muscle cells (e.g., smooth muscle cells, skeletal muscle cells, myocardial cells), neurocytes (e.g., glia cells, schwan cells, myelin sheath cells), hematopoietic cells, mast cells, hepatocytes, hepatic parenchymal cells, and bone marrow cells. Examples of stem cells include, but are not limited to, embryonic stem cells (ESCs), pluripotent stem cells, induced pluripotent stem cells, embryonic stem cells, adult stem cells, and multipotent and induced multipotent stem cells such as neural cells, mesencymal stem cells, epithelial stem cells, bone marrow stem cells, neural stem cells, hematopoietic stem cells, germ stem cells, somatic stem cells, modified stem cells, and the like.

Various media can be used for the cell cultures of this disclosure, including, but not limited to BD Matrigel™ (manufactured by Becton, Dickinson and Company), ReproFF (manufactured by ReproCELL Incorporated), and the like. Other reagents, and materials may also be used for the cell culture based on the type of cells to be cultured.

When one or more cultured cells are ready to be harvested, the method includes, at 304, radiating a first optical energy onto at least some of the support molecules so that the photoresponsive region of the at least some support molecules changes conformation to a more hydrophilic state than the more hydrophobic state.

As illustratively discussed above, radiating the first optical energy may be performed at a particular combination of wavelength, power, time period, and/or distance. In addition to the illustrative examples of wavelength, power, time period, and/or distance described above, in one embodiment, radiating the first optical energy onto at least some of the molecules is performed in phases. This can include a first phase having a first light wavelength, a first light intensity, and a first time period configured to cause the at least some of the molecules to conform to a first conformation that is more hydrophilic than the more hydrophobic state. This embodiment can also include a second phase having a second light wavelength, a second light intensity, and a second time period configured to cause the at least some of the molecules to conform to a second conformation that is more hydrophilic than the first conformation.

As also described above, an optical device can be arranged so that portions of the support molecules can be irradiated independently from other portions of the molecules. Other embodiments will be understood from the disclosure herein and will not be described in further detail to avoid obscuring the concepts herein. Further, the amount of culturing time depends on the type of cells to be cultures.

Because at least a portion of the support molecules have been irradiated to conform to a second conformation, the surface of the support layer changes to be more hydrophilic to unadhere, detached, or disconnect the cultured cells from that portion of the support layer.

The method includes, at 306, harvesting one or more cultured cells from the support molecules. Various known culture methods may be used depending on the type of the cells that are cultured. Harvesting can include using pipetting, filtering, centrifugation, cell sorting, glass capillary/colony cutter (e.g., STEMPRO EZpassage), and the like. Alternatively or additionally, when a cluster of cells are cultured for producing tissue such as skin or other organs, the cells can be collected using tweezers or other conventional tools.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An apparatus for cell culture comprising:
a substrate;

a support layer at least partially coating the substrate, the support layer comprised of support molecules having a first region configured to bind to the substrate and having a plurality of photo-responsive regions configured to change conformation responsive to irradiation from at least a first optical energy source, wherein the support molecules are azobenzene compounds having a formula of:

wherein R is $C_8H_{17}$ and R' is $OCH_2COOH$;
wherein in a first conformation of the plurality of photo-responsive regions, the support molecules are in a more hydrophobic state displaying a diazo functional group (N═N) on a top surface of the support molecules configured to be more accessible to cells;
wherein in a second conformation of the plurality of photo-responsive regions, the support molecules are in a more hydrophilic state displaying polar groups on the top layer of the support molecules, while the diazo functional group is configured to be less accessible to cells; and
an array of optical elements covering substantially all of one surface of the substrate so as to permit irradiation of the support layer, wherein the array of optical elements are operably coupled to the first optical energy source, each of the optical elements of the array of optical elements configured to be operated independently of each other to selectively irradiate the plurality of photo-responsive regions.

2. The apparatus as recited in claim 1, wherein the plurality of photo-responsive regions of the molecules includes one or more groups that alter conformation upon irradiation from the first optical energy source.

3. The apparatus as recited in claim 1, wherein the array of optical elements is configured to irradiate a light in a wavelength of about 400 nm to about 500 nm.

4. The apparatus as recited in claim 1, wherein the array of optical elements is configured to irradiate a light having a power of about 1 $mW/cm^2$ to about 100,000 $mW/cm^2$.

5. The apparatus as recited in claim 1, wherein the array of optical elements is configured to irradiate a light for about 0.1 s to about 10,000 s.

6. The apparatus as recited in claim 1, wherein the array of optical elements is configured to irradiate a light at a distance of about 1 cm to about 200 cm from the support layer.

7. The apparatus as recited in claim 1, wherein the cells accessing the plurality of photo-responsive regions are one or more of stem cells, osteocyte cells, epidermal cells, organ cells, tissue engineering cells, pluripotent cells, pluripotent stem cells, multipotent stem cells, hematopoietic stem cells, mesenchymal stem cells, epithelial stem cells, bone marrow stem cells, germ stem cells, somatic stem cells, modified stem cells, or a combination thereof.

8. An apparatus for cell culture comprising:
a substrate;
a support layer at least partially coating the substrate, the support layer comprised of support molecules having a first region configured to bind to the substrate and having a plurality of photo-responsive regions configured to change conformation responsive to irradiation from at least a first optical energy source, wherein the support molecules are azobenzene compounds having a formula of:

wherein R is $C_8H_{17}$ and R' is a polar functional group;
wherein in a first conformation of the plurality of photo-responsive regions, the support molecules are in a more hydrophobic state displaying a diazo functional group (N═N) on a top surface of the support molecules configured to be more accessible to cells;
wherein in a second conformation of the plurality of photo-responsive regions, the support molecules are in a more hydrophilic state displaying polar groups on the top layer of the support molecules, while the diazo functional group is configured to be less accessible to cells; and
an array of optical elements covering substantially all of one surface of the substrate so as to permit irradiation of the support layer, wherein the array of optical elements are operably coupled to the first optical energy source, each of the optical elements of the array of optical elements configured to be operated independently of each other to selectively irradiate the plurality of photo-responsive regions.

9. The apparatus as recited in claim 8, wherein the plurality of photo-responsive regions of the molecules includes one or more groups that alter conformation upon irradiation from the first optical energy source.

10. The apparatus as recited in claim 8, wherein the array of optical elements is configured to irradiate a light in a wavelength of about 400 nm to about 500 nm.

11. The apparatus as recited in claim 8, wherein the array of optical elements is configured to irradiate a light having a power of about 1 mW/cm$^2$ to about 100,000 mW/cm$^2$.

12. The apparatus as recited in claim 8, wherein the array of optical elements is configured to irradiate a light for about 0.1 s to about 10,000 s.

13. The apparatus as recited in claim 8, wherein the array of optical elements is configured to irradiate a light at a distance of about 1 cm to about 200 cm from the support layer.

14. The apparatus as recited in claim 8, wherein the cells accessing the plurality of photo-responsive regions include stem cells, osteocyte cells, epidermal cells, organ cells, tissue engineering cells, pluripotent cells, pluripotent stem cells, multipotent stem cells, hematopoietic stem cells, mesenchymal stem cells, epithelial stem cells, bone marrow stem cells, germ stem cells, somatic stem cells, modified stem cells, or combinations thereof.

15. The apparatus as recited in claim 8, wherein R' is OCH$_2$COOH.

16. An apparatus for cell culture comprising:
 a substrate;
 a support layer at least partially coating the substrate, the support layer comprised of azobenzene support molecules including:
  a first region bound to the substrate by C$_8$H$_{17}$; and
  a plurality of photo-responsive regions including:
   diazo functional groups of the azobenzene molecules, the diazo functional groups being configured to change conformation responsive to irradiation from at least a first optical energy source;
   diarylethene groups configured to change conformation responsive to irradiation from at least the first optical energy source
   wherein the plurality of photo-responsive regions terminate in a polar functional group;
  wherein in a first conformation of the plurality of photo-responsive regions, the support molecules are in a more hydrophobic state configured to be conducive to cell adherence thereto;
  wherein in a second conformation of the plurality of photo-responsive regions, the support molecules are in a more hydrophilic state configured to be less conducive to cell adherence than the first confirmation; and
 an array of optical elements covering substantially all of one surface of the substrate so as to permit irradiation of the support layer, wherein the array of optical elements are operably coupled to the first optical energy source, each of the optical elements of the array of optical elements configured to be operated independently of each other to selectively irradiate the plurality of photo-responsive regions.

17. The apparatus as recited in claim 16, wherein the polar functional group is OCH$_2$COOH.

* * * * *

UNITED STATES PATENT AND TRADEMARK OFFICE
CERTIFICATE OF CORRECTION

PATENT NO. : 9,080,140 B2  
APPLICATION NO. : 12/628850  
DATED : July 14, 2015  
INVENTOR(S) : Ueda Page 1 of 1

It is certified that error appears in the above-identified patent and that said Letters Patent is hereby corrected as shown below:

On the Title Page, in Item (56), under "OTHER PUBLICATIONS", in Column 1, Line 1, delete "Enclyclopaedia Britannica." and insert -- Encyclopedia Britannica. --, therefor.

Specification

In Column 10, Line 2, delete "about 0.1" and insert -- about 0.1 s --, therefor.

Signed and Sealed this  
Twenty-third Day of February, 2016

Michelle K. Lee  
*Director of the United States Patent and Trademark Office*